United States Patent [19]
Stankowiak et al.

[11] Patent Number: 6,059,989
[45] Date of Patent: May 9, 2000

[54] DEICING COMPOSITION BASED ON ACETATES AND/OR FORMATES, AND METHOD FOR MELTING SNOW AND ICE ON TRAFFIC AREAS WITH THE AID OF SAID COMPOSITION

[75] Inventors: Achim Stankowiak, Altötting; Wilfried Becker, Neuötting, both of Germany

[73] Assignee: Clariant GmbH, Frankfurt, Germany

[21] Appl. No.: 09/194,932

[22] PCT Filed: May 30, 1997

[86] PCT No.: PCT/EP97/02810

§ 371 Date: Dec. 4, 1998

§ 102(e) Date: Dec. 4, 1998

[87] PCT Pub. No.: WO97/47703

PCT Pub. Date: Dec. 18, 1997

[30] Foreign Application Priority Data

Jun. 7, 1996 [DE] Germany ............ 196 22 857
Nov. 25, 1996 [DE] Germany ............ 196 48 716

[51] Int. Cl.⁷ ....................................... C09K 3/18
[52] U.S. Cl. ................................. 252/70; 106/13
[58] Field of Search ................... 106/13; 252/70

[56] References Cited

U.S. PATENT DOCUMENTS

| | | | |
|---|---|---|---|
| 4,803,007 | 2/1989 | Garber | 252/70 |
| 5,064,551 | 11/1991 | Smith | 252/70 |
| 5,127,954 | 7/1992 | Johnston et al. | 106/644 |
| 5,350,533 | 9/1994 | Hubred et al. | 252/70 |
| 5,435,930 | 7/1995 | Chan et al. | 508/145 |

FOREIGN PATENT DOCUMENTS

| | | |
|---|---|---|
| 375 214 | 6/1990 | European Pat. Off. |
| 494 506 | 7/1992 | European Pat. Off. |
| 40 34 217 | 5/1991 | Germany |
| 94/17152 | 8/1994 | WIPO |

*Primary Examiner*—Anthony Green
*Attorney, Agent, or Firm*—Miles B. Dearth

[57] ABSTRACT

The deicing composition described consists essentially of a) from 87 to 99.45% by weight of an alkali metal acetate or an alkali metal formate or a mixture thereof, b) from 0.5 to 10% by weight of an alkali metal silicate, and c) from 0.05 to 3% by weight of an alkali metal phosphate. It can be employed in solid form (powder, granules and the like) or in the form of an aqueous solution. It ensures a short thaw time and corrosion protection, especially with regard to magnesium.

4 Claims, No Drawings

6,059,989

1

DEICING COMPOSITION BASED ON ACETATES AND/OR FORMATES, AND METHOD FOR MELTING SNOW AND ICE ON TRAFFIC AREAS WITH THE AID OF SAID COMPOSITION

FIELD OF THE INVENTION

The invention relates to a deicing composition based on alkali metal acetates, alkali metal formates or a mixture of the two for traffic areas. The invention also relates to a method of melting snow and ice on traffic areas using said composition.

DESCRIPTION OF THE RELATED ART

Snow and/or ice on roads, cycleways, footpaths, bridges, sportsgrounds, airfields and the like (called traffic areas below) lead to a substantial impairment in the progress of the traffic and in transport safety. It has therefore long been known to apply to such areas a composition for melting or thawing snow and ice.

The requirements to be met by a deicing composition are multifaceted. The materials from which the areas in question are constructed, for example concrete, must not be damaged, let alone destroyed, by the deicing composition. It is also essential to rule out a corrosive action on metals, inter alia. Since the composition may enter the wastewater, biodegradability is a further requirement. It is also essential that very rapid thawing is achieved. From the economic standpoint, finally, it is necessary that only a small amount of deicing composition is required and that it does not cost much.

The prior art describes numerous alkali metal salts and alkaline earth metal salts of inorganic and organic acids as deicing agents, examples being sodium chloride, calcium chloride, sodium formate, calcium formate, sodium acetate, magnesium acetate, sodium lactate and the like. These deicing agents, especially the acetates and formates, do indeed meet several of the abovementioned requirements; however, with regard to corrosion they leave much to be desired. For instance, especially on light metals such as aluminum and magnesium, they have a more or less strong corrosive effect, which is particularly disadvantageous in view of means of transport such as cars, motorbikes, aircraft and the like.

Attempts have already been made to solve the abovementioned problems with the aid of inhibitors. Thus EP-A 0 375 214 describes a liquid deicer consisting essentially of from 45 to 60% by weight of an alkali metal acetate and/or alkali metal formate, from 0.1 to 0.4% by weight of an alkali metal phosphate, from 0.2 to 0.6% by weight of an alkali metal nitrite, and water as a remainder to 100% by weight, the percentages by weight being based on the weight of the deicer. However, the inhibitor effect of alkali metal phosphate and alkali metal nitrite leaves much to be desired, especially with regard to magnesium; a further disadvantage is the nitrite content.

DE-A 40 34 217 describes a liquid or solid deicing composition based on water-soluble alkali metal salts of formic acid and/or acetic acid, the corrosion inhibitor system consisting of water-soluble polycarboxylic acids and water-soluble silicates and/or carbonates of alkali metals or of ammonium. This chloride- and nitrite-free deicing composition is said to attack neither constructions of concrete, bitumen or stone, nor metallic materials such as iron, copper, aluminum or zinc. The anticorrosive effect is based on the combination of a water-soluble polycarboxylic acid, such as succinic acid, citric acid or tartaric acid, with a water-soluble silicate and/or carbonate. In the case of light metals, it too leaves much to be desired.

2

Mention may also be made of U.S. Pat. No. 4,803,007, in which a deicing composition is described which is based on sodium chloride and which employs, as corrosion inhibitor, a mixture of a divalent metal salt and an alkali metal polyphosphate. Divalent metals mentioned include calcium, magnesium and barium and, as counterions, borates, metasilicates and sulfates. This inhibitor combination acts in particular to counter corrosion to ferrous metals, but less so with respect to the corrosion of light metals such as magnesium.

SUMMARY OF THE INVENTION

It has now been found that a mixture of alkali metal phosphates and alkali metal silicates is a particularly effective light metal corrosion inhibitor for a deicing composition based on alkali metal salts of formic acid and/or acetic acid.

The novel deicing composition consists essentially of a) from 87 to 99.45% by weight, preferably from 92 to 97.9% by weight, of an alkali metal acetate and/or alkali metal formate, b) from 0.5 to 10% by weight, preferably from 2 to 7% by weight, of an alkali metal silicate, and c) from 0.05 to 3% by weight, preferably from 0.1 to 1% by weight, of an alkali metal phosphate.

DESCRIPTION OF THE PREFERRED EMBODIMENTS

Component a) is preferably an alkali metal formate. Among the water-soluble alkali metal formates, and the acetates as well, preference is given to those of sodium and potassium. Component a) is therefore, preferably, a sodium formate and/or potassium formate.

Component b) is a water-soluble alkali metal silicate, the alkali metal again being preferably sodium or potassium. Suitable representatives are the orthosilicates (mono-, di-, tri- and tetrabasic), disilicates to tetrasilicates, and/or the water-soluble metasilicates, which are preferred.

Component c) is a water-soluble alkali metal salt of phosphoric acid. It can be a mono-, di- or tribasic alkali metal phosphate, the alkali metal preferably being sodium or potassium.

The novel deicing composition is prepared by mixing the liquid or solid components together. The deicing composition can therefore be employed in solid form, for example as a powder or granules, or as an aqueous solution. The amounts of the three components, with or without further advantageous components, in the aqueous deicing composition (overall concentration) can be varied within wide limits. It depends in particular on the solubility of the components in water (the solution should be essentially clear). With a relatively concentrated solution a smaller amount will be required, for thawing ice and/or snow, than with a less concentrated one. The preferred concentration, accordingly, is from 15 to 70% by weight, preferably from 25 to 60% by weight, percentages by weight being based on the weight of the solution. The pH of the aqueous deicing composition is in general from 7 to 10. Where this pH is not already present after the components have been mixed together, it will be established at the desired value by adding, preferably, an alkali metal hydroxide, such as sodium hydroxide or potassium hydroxide.

The novel method of melting snow and ice on traffic areas comprises applying an effective amount of the above-described deicing composition (in solid or liquid form) to the traffic area that is to be treated; in other words, an amount such that the target elimination of ice and/or snow is achieved. This amount depends in particular on the external temperature and on the amount of ice and/or snow present, and in general is from 10 to 100 g per m² of ice- and/or snow-covered area. The application of the liquid deicing composition can be implemented, for example, with the aid of the customary spraying vehicles.

The novel deicing composition possesses a series of advantages. For instance, it meets the requirements set out at the outset and features not only a short thaw time but also an unexpectedly high level of inhibition of metallic corrosion, especially of magnesium. This results apparently from the combination of the abovementioned phosphates and silicates each in a defined amount and from the fact that this inhibitor system is highly active specifically in the case of alkali metal acetates and/or formates. The novel deicing composition is free from chloride and nitrite and is also particularly suitable for aircraft traffic areas such as runways (take off and landing), parking areas, bus routes and the like. It is preferably employed in solid form (powder, granules and the like).

The invention will now be illustrated in more detail with reference to novel examples and comparison examples.

The deicing compositions of novel Examples 1 to 5 and of Comparison Examples 1 to 3 below were prepared by mixing the components. The stated percentages for the individual components are percentages by weight.

EXAMPLE 1

97.8% sodium formate
2.0% sodium metasilicate
0.2% tripotassium phosphate

EXAMPLE 2

92.0% potassium formate
7.0% sodium metasilicate
1.0% tripotassium phosphate

EXAMPLE 3

90.0% sodium formate
8.0% potassium metasilicate
2.0% tripotassium phosphate

EXAMPLE 4

96.5% sodium formate
0.5% sodium metasilicate
3.0% trisodium phosphate

EXAMPLE 5

87.0% sodium formate
10.0% sodium metasilicate
3.0% dipotassium hydrogen phosphate

COMPARISON EXAMPLE 1

97.8% sodium formate
2.0% calcium metasilicate
0.2% tripotassium phosphate

COMPARISON EXAMPLE 2

99.0% sodium formate
0.5% sodium metasilicate
0.5% citric acid

COMPARISON EXAMPLE 3

97.8% sodium chloride
2.0% calcium metasilicate
0.2% tripotassium phosphate

The deicing compositions of Examples 1 to 5 and of Comparison Examples 1 to 3 were tested for magnesium corrosion. The test was in accordance with ASTM F483 (ASTM=American Society for Testing and Materials). In this test, the weighed test specimen is immersed for 24 hours under atmospheric pressure in the test deicing composition, which is held at a temperature of 35° C., after which the weight of the test specimen is measured again. The result of the corrosion test is stated as the difference in weight between the two measurements, in milligrams per cm² of test specimen per 24 hours. The test was carried out with magnesium AMS 4374 (chromated) and with 15% strength by weight aqueous solutions of the deicing compositions indicated. The results are compiled in the table below and indicate that the novel deicing compositions are very well inhibited with regard to magnesium corrosion. As far as the thaw time of the novel deicing compositions is concerned, they meet the required rapid thawing of ice and snow. The novel deicing compositions therefore possess a surprisingly high degree of inhibition with respect to magnesium corrosion, and the required short thaw time.

TABLE

Test results of magnesium corrosion in accordance with ASTM F483 in milligrams of weight difference per cm² of test specimen per 24 hours

| | 15% strength by weight aqueous solution [mg] |
|---|---|
| Example | |
| 1 | −0.1 |
| 2 | −0.1 |
| 3 | −0.2 |
| 4 | −0.2 |
| 5 | −0.1 |
| Comparison Example | |
| 1 | −14.7 |
| 2 | −2.4 |
| 3 | −7.1 |

We claim:

1. A deicing composition consisting essentially of
   a) from 87 to 99.45% by weight of an alkali metal acetate or an alkali metal formate or a mixture thereof,
   b) from 0.5 to 10% by weight of an alkali metal silicate, and
   c) from 0.05 to 3% by weight of an alkali metal phosphate.

2. The deicing composition as claimed in claim 1, consisting essentially of
   a) from 92 to 97.9% by weight of an alkali metal acetate or an alkali metal formate or a mixture thereof,
   b) from 2 to 7% by weight of an alkali metal silicate, and
   c) from 0.1 to 1% by weight of an alkali metal phosphate.

3. The deicing composition as claimed in claim 1, wherein component a) is an alkali metal formate, component b) is a metasilicate and component c) is a mono-, di- or tribasic alkali metal phosphate.

4. A method of melting ice and snow on traffic areas, which comprises applying an effective amount of the deicing composition as claimed in claim 1, in solid form or in the form of an aqueous solution, to the traffic areas.

* * * * *